United States Patent [19]

Amigues et al.

[11] 4,132,745
[45] Jan. 2, 1979

[54] PROCESS FOR ISOMERIZING 1-BUTENE TO 2-BUTENE

[75] Inventors: Pierre Amigues, La Muladiere; Jean Gaillard, Carrieres; Jean-Francois Le Page, Rueil Malmaison; Robert Stern, Paris, all of France

[73] Assignee: Institut Francais du Petrole, Rueil-Malmaison, France

[21] Appl. No.: 879,579

[22] Filed: Feb. 21, 1978

Related U.S. Application Data

[63] Continuation-in-part of Ser. No. 809,812, Jun. 24, 1977, abandoned.

[30] Foreign Application Priority Data

Jun. 25, 1976 [BE] Belgium ................................. 19661

[51] Int. Cl.$^2$ ............................ C07C 5/24; C07C 5/30
[52] U.S. Cl. .................................................. 260/683.2

[58] Field of Search ..................................... 260/683.2

[56] References Cited

U.S. PATENT DOCUMENTS

| | | | |
|---|---|---|---|
| 3,630,961 | 12/1971 | Wilhelm ............................. | 260/683.2 |
| 3,632,525 | 1/1972 | Rausch .............................. | 260/683.2 |
| 3,772,400 | 11/1973 | Garner et al. ...................... | 260/683.2 |

*Primary Examiner*—Veronica O'Keefe
*Attorney, Agent, or Firm*—Millen & White

[57] ABSTRACT

Process for isomerizing 1-butene to 2-butene by contacting 1-butene, at a temperature from 50 to 140° C, in the presence of hydrogen, with an isomerization catalyst containing a noble metal from group VIII of the periodic classification of elements, which catalyst was previously contacted with a sulfur compound at a temperature from 50 to 400° C and then with hydrogen at a temperature of at least 50° C.

19 Claims, No Drawings

PROCESS FOR ISOMERIZING 1-BUTENE TO 2-BUTENE

This application is a continuation-in-part of our prior U.S. patent application Ser. No. 809,812 filed June 24, 1977 now abandoned.

This invention concerns a process for isomerizing 1-butene to 2-butene. Various chemical processes, for example cracking of petroleum fractions, produce $C_4$ cuts containing a substantial proportion of 1-butene. However, for some kinds of use, it is preferred to obtain a high content of 2-butene. A first object of the invention is, accordingly, to isomerize 1-butene to 2-butene.

In some charges butadiene is also present. It is therefore advantageous to separate it by known means, for example by distillation or extraction with a polar solvent. However, even after this treatment, a noticeable proportion of residual butadiene is still present with traces of the polar solvent used for the extraction, said traces being sufficient for progressively poisoning the catalyst. Accordingly, a second object of the invention is to carry out simultaneously the hydrogenation of the residual butadiene and the isomerization of 1-butene to 2-butene without noticeable deactivation of the catalyst.

It has already been proposed to carry out these reactions by contacting 1-butene or a mixture of 1-butene and butadiene (which may contain other hydrocarbons, for example butane, isobutane, 2-butene and isobutene) with a palladium on alumina catalyst under hydrogen atmosphere.

Several difficulties have occured, as mentioned in the U.S. Pat. No. 3,531,545, particularly:

—excessive hydrogenation, leading to a substantial olefin loss,

—polymerization of the highly unsaturated hydrocarbons, resulting in a deactivation of the catalyst.

U.S. Pat. No. 3,531,545 has for object to solve these problems by adding sulfur compounds to the hydrocarbon charge. This strongly reduces the activity of the catalyst and obliges to proceed at high temperature, from 135° to 260° C., preferably from 163° to 190° C., to maintain acceptable reaction rates; at these high temperatures, the thermodynamic equilibrium is unfavorable to the conversion of 1-butene to 2-butene. Moreover, even when sulfur is present in the feedstock, isobutene polymerizes, as shown, for example, in example 1 (run numbers 1 and 2) of U.S. Pat. No. 3,772,400, thereby reducing the selectivity of the isomerization reaction. To remedy this, the latter patent has recourse to a pretreatment of the catalyst with a nitrogen compound. Finally, in the presence of sulfur, it is usually necessary to make use of a high proportion of hydrogen and to remove sulfur at the end of the operation.

The present invention obviates the inconveniences of the above processes. It provides for the isomerization of 1-butene at a lower temperature than according to the prior processes and, accordingly, it results in a more complete conversion thereof to 2-butene. The reaction velocity is high even at said relatively low temperature. The hydrogenation of olefins to saturated hydrocarbons is negligible. The sensitivity of the catalysts to poisons is reduced as compared with the use of noble metals without the pre-treatment of the invention. Finally, the polymerization reactions are inhibited.

The process for isomerizing 1-butene, according to the invention, comprises the following 2-step pretreatment:

(a) contacting a sulfur compound with an isomerization catalyst containing a noble metal from group VIII, and (b) subsequently contacting the catalyst with hydrogen.

The catalyst resulting from step (b) may then be used to isomerize 1-butene to 2-butene, in the presence of hydrogen.

As above-mentioned, 1-butene may be used alone or in admixture with one or more hydrocarbons, particularly one or more of the following hydrocarbons:

butadiene
2-butene (cis and/or trans)
isobutene
butane and isobutane

When butadiene is present, it is hydrogenated to butene, which is an advantage of the process.

The presence, in the charge, of compounds capable of deactivating the catalyst or making it more selective, for example sulfur compounds or nitrogen, is undesirable; as a matter of fact, as above mentioned, the presence of such compounds requires high operating temperatures which are unfavorable to the isomerization. It is accordingly preferred to make use of a charge containing not more than 10 ppm b.w. of sulfur, preferably less than 5 ppm by mole of sulfur (1 mole sulfur = 32 g), more preferably less than 1 ppm by mole of sulfur. The charge preferably contains not more than 10 ppm b.w. nitrogen, preferably less than 5 ppm by mole, more preferably less than 1 ppm by mole.

The isomerization temperature is usually from 50 to 140° C., preferably from 65° to 120° C. and still more preferably from 70° to 110° C. The lower the temperature, the more favorable the thermodynamic equilibrium to the production of a high proportion of 2-butene.

The pressure may be selected in a wide range, for example about 1 to 50 relative atmospheres and preferably 5 to 30 relative atmospheres. The best results have been obtained by maintaining 1-butene or at least a major part thereof in the liquid phase and, preferably, substantially entirely in the liquid phase. The pressure may be supplied by hydrogen or a mixture of hydrogen with an inert gas. The feed rate of 1-butene is usually from 1 to 50, preferably from 5 to 20 liters (in the liquid state) per liter of catalyst and per hour. Hydrogen is generally used at a rate of 0.1 to 15 moles percent, preferably 1 to 10 moles percent, with respect to 1-butene or to the mixture of 1-butene with butadiene.

The catalyst comprises at least one noble metal from group VIII, i.e. ruthenium, rhodium, palladium, osmium, iridium and/or platinum, preferably at a concentration of 0.01–2% b.w. on a carrier. Palladium is preferred in view of its higher selectivity. Any one of the usual carriers may be used, for example alumina (preferred carrier), silica-alumina and carbon, and the catalyst is preferably of the fixed bed type. A preferred catalyst comprises 0.01 to 2% by weight of palladium on alumina. The invention is not limited to a particular type of noble metal catalyst. There can be used commercial catalysts, for example LD-265 or LD 269 of Societe Francaise des Produits pour Catalyse (PROCATALYSE).

According to the invention, this catalyst is treated with a sulfur compound and then with hydrogen before use. It is however unnecessary that the catalyst metal be in a reduced state when carrying out this treatment, it is also possible to proceed with the catalyst containing the noble metal in the form of a compound, for example as oxide. Whenever possible, at least 1 gram-atom of sulfur per gram-atom of noble metal is to be used. Preferably there is used at least 2 gram-atoms of sulfur, for example from 5 to 10 gram-atoms or more, per gram-atom of noble metal. These amounts are those which are passed through the catalyst bed, although not all sulfur effectively combines with the catalyst.

According to a preferred technique, the sulfur compound is allowed to flow until it is no longer retained by the catalyst. The temperature of this treatment is usually higher than 20° C., for example from 50° to 400° C. or more, preferably from 80° to 130° C. The sulfur compound may be used alone or diluted in a gas such as nitrogen, methane, argon or preferably hydrogen. It is also possible to introduce the sulfur compound in the liquid phase as a solution in a hydrocarbon solvent. In any case (gas or liquid phase), the concentration of the sulfur compound is preferably at least 0.1% sulfur by weight.

The sulfur compound may be any one of those described in the U.S. Pat. No. 3,531,545; it is however preferred to make use of hydrogen sulfide. Its partial pressure is, for example, from 0.01 to 10 atmospheres. A preferred sulfiding mixture comprises 0.1–10% $H_2S$ by volume, the remainder being preferably hydrogen.

The duration of the treatment with the sulfur compound is not critical, provided that a substantial amount of sulfur is supplied to the catalyst. The usual duration of the treatment is at least 5 minutes, for example from 5 minutes to 6 hours. At the end of this treatment, the catalyst has lost a large part of its initial activity.

The second step of the catalyst treatment according to the invention, is a treatment with hydrogen of the presulfided catalyst as above-described. During this treatment the catalyst regains a large part of its initial activity while being much more selective. The treatment may thus be followed by testing the activity of the catalyst.

Although the limit conditions of this treatment are not completely known, it seems that the best results are obtained when proceeding at 50° C. or more, for example at 50°–250° C. or more, preferably above 80° C. The contact time is usually at least 10 minutes, for example from 10 minutes to 10 hours. The hydrogen pressure is, for example, from 0.1 to 10 atmospheres or more. Hydrogen may be used in the pure state or diluted in an inert gas, for example methane.

Substantially sulfur-free hydrogen gas is preferred (for example less than 100 ppm sulfur b.w., preferably less than 1 ppm b.w.). This treatment is preferably conducted in the absence of the hydrocarbon charge to be isomerized. The treatment may be inspected by analyzing the effluent gas; it is preferably interrupted when this gas no more strips sulfur from the catalyst.

It is preferred to avoid a too severe or too lengthy treatment with hydrogen; as a matter of fact, in the case of a too severe treatment, the hydrogenating activity of the catalyst becomes excessive and may be detrimental to the selectivity of the isomerization. That is why a temperature of 80°–160° C. is preferred. The following examples indicate particularly favorable conditions for carrying out this treatment.

The following non limitative examples illustrate the invention.

EXAMPLE 1 (PREPARATION OF THE CATALYST)

80 g of catalyst consisting of 0.5% by weight of palladium on alumina, in fixed bed, is heated to a temperature of 100° C. under hydrogen atmosphere (1 atmosphere). At the same temperature and the same pressure, 80 liters of hydrogen containing 2% by volume of hydrogen sulfide are passed over the catalyst for 2 hours. At the end, $H_2S$ is substantially no more retained by the catalyst. The temperature is then increased to 130° C. and sulfur-free hydrogen is passed under 1 atmosphere for 6 hours at a rate of 40 liters per hour. At the end substantially no more sulfur is present in the off-gas. The catalyst is then ready for use.

EXAMPLE 2

Over 20 cc of the so-prepared catalyst, sulfur-free hydrogen is passed with a mixture of 99.66% of 1-butene and 0.34% of n-butane at the temperature of 80° C., under a relative pressure of 25 atmospheres. The hydrocarbon flow rate (VVH) is 5 volumes per volume of catalyst and per hour, that of hydrogen is 1 liter per hour. There is obtained an effluent whose analysis by volume is as follows:

1-butene: 10.9%
2-butene: 87%
n-butane: 2.1%

No polymer was formed.

EXAMPLE 3

Example 2 is repeated with a charge whose analysis is given in table I. The temperature is 100° C., the relative pressure 25 atmospheres, the VVH 10, 20 or 40 and the hydrogen flow rate respectively 2, 4 and 8 liters per hour. The results are reported in table I.

TABLE I

| Composition of the charge % by weight | | Composition of the product % by weight | | |
|---|---|---|---|---|
| | | VVH = 10 | VVH = 20 | VVH = 40 |
| isobutane | 1.40 | 1.40 | 1.40 | 1.30 |
| n-butane | 12.0 | 13.7 | 13.75 | 13.90 |
| butene-1 | 49.47 | 5.93 | 7.35 | 11.66 |
| isobutene | 2.68 | 2.8 | 2.80 | 2.80 |
| butene-2 trans | 21.47 | 48.26 | 46.8 | 43.95 |
| butene-2 cis | 12.62 | 27.90 | 27.90 | 26.40 |
| butadiene | 0.36 | <5 ppm | <5 ppm | <5 ppm |

No polymer had formed.

EXAMPLE 4

Example 2 is repeated with the charge of high isobutene and butadiene contents, whose composition is given in table II.

The pressure is 15 atmospheres, the temperature 80° C., the VVH is 10 and the hydrogen flow rate 3 liters per hour.

TABLE II

| Composition of the charge % by weight | | Composition of the product % by weight |
|---|---|---|
| isobutane | 1.70 | 1.75 |
| n butane | 9.25 | 11.19 |
| butene-1 | 25.7 | 2.50 |
| isobutene | 47.1 | 47.00 |
| butene-2 trans | 10.4 | 25.46 |
| butene-2 cis | 5.3 | 12.10 |
| butadiene | 0.55 | <5 ppm |

No polymer formation was observed.

EXAMPLE 5 (FOR COMPARATIVE PURPOSE)

There is used a catalyst consisting of 0.5% of reduced palladium on alumina. Over this catalyst, in fixed bed, there is passed a charge whose composition is given in table III and to which hydrogen sulfide was added in a proportion of 100 parts per million of parts by weight.

The conditions were the following:
Temperature: 80° C., VVH: 5
Pressure: 25 kg/cm$^2$, Hydrogen flow rate: 40 liters per hour and per liter of catalyst.

After 48 hours, the effluent is analyzed and substantially no isomerization is observed.

This example shows that isomerization does not occur at 80° C. when the feedstock has a relatively high sulfur content.

EXAMPLE 6 (COMPARATIVE)

Example 5 is continued but H$_2$S is no more introduced.

The effluent is analyzed after 48 hours. The analysis, given in table III, shows that the isomerization rate is low, this being attributable to the presence of sulfur previously retained (example 5) by the catalyst.

EXAMPLE 7

The catalyst resulting from example 6 is treated with hydrogen at 135° C. under atmospheric pressure, the hydrogen flow rate being 400 liters per hour and per liter catalyst.

After 6 hours of this treatment, the isomerization is again performed under the conditions of example 6, i.e. at 80° C., 25 kg/cm$^2$, VVH 5 and 40 liters H$_2$/hour/liter of catalyst (in the absence of H$_2$S).

After 48 hours, the analysis of the product gives the results reported in table III.

TABLE III

| | COMPOSITION (% by weight) | | |
|---|---|---|---|
| | Starting charge | Sulfurized catalyst (example 6) | Desulfurized catalyst (example 7) |
| isobutane | 1.73 | 1.75 | 1.70 |
| n butane | 9.93 | 11.16 | 11.15 |
| butene-1 | 54.05 | 39.02 | 4.85 |
| butene 2 trans | 22.16 | 28.09 | 51.10 |
| butene 2 cis | 12.0 | 19.89 | 31.20 |
| butadiene | 0.13 | 0.09 | < 5 ppm |

No polymer formed.

What we claim is:

1. In a process for isomerizing 1-butene, wherein a hydrocarbon charge containing 1-butene and hydrogen is contacted with a Group VIII noble metal catalyst, at an isomerization temperature, the improvment wherein the catalyst results from the previous steps of:
   (a) passing a gas or a liquid providing a sulfur compound at a concentration of at least 0.1% sulfur b.w. through a bed of catalyst consisting essentially of a Group VIII noble metal at a temperature of 20°–400° C. for a sufficient time to pass therethrough at least 1 gram-atom sulfur per gram-atom of Group VIII noble metal, and then continuing said passing until substantially no more sulfur compound is retained by the catalyst,
   (b) contacting the catalyst with substantially sulfur-free hydrogen at a temperature of at least 50° C., thereby obtaining a catalyst of both high activity and selectivity.

2. A process according to claim 1, wherein the Group VIII noble metal catalyst comprises 0.01–2% b.w. palladium on alumina.

3. A process according to claim 1, wherein step (a) is conducted at 80°–130° C. for at least 5 minutes.

4. A process according to claim 1, wherein the sulfur compound in step (a) is hydrogen sulfide.

5. A process according to claim 4, wherein the partial pressure of hydrogen sulfide is 0.01–10 atmospheres.

6. A process according to claim 4, wherein hydrogen sulfide is used in admixture with hydrogen.

7. A process according to claim 6, wherein the admixture comprises 0.1–10% by volume of hydrogen sulfide.

8. A process according to claim 1, wherein step (a) is conducted for 5 minutes to 6 hours.

9. A process according to claim 1, wherein step (a) is continued for sufficient time to provide at least 2 gram-atoms of sulfur per gram-atom of noble metal.

10. A process according to claim 1, wherein step (b) is effected at 50°–250° C. for at least 10 minutes.

11. A process according to claim 1, wherein step (b) is effected at above 80° C.

12. A process according to claim 1, wherein the hydrocarbon charge contains at most 10 ppm by weight of sulfur.

13. A process according to claim 1, wherein the hydrocarbon charge contains at most 1 ppm by mole of sulfur.

14. A process according to claim 1, wherein the hydrocarbon charge also comprises butadiene.

15. A process according to claim 1, wherein the isomerization temperature is 65°–120° C.

16. A process according to claim 1, wherein 1-butene is at least in major part in the liquid phase, the liquid flow rate of said 1-butene being at least 5 volumes per volume of catalyst per hour.

17. A process according to claim 12, wherein the isomerization temperature is 65°–120° C.

18. A process according to claim 12, wherein the isomerization temperature is 50°–140° C.

19. A process according to claim 12, wherein the isomerization temperature is 70°–110° C.

* * * * *

UNITED STATES PATENT AND TRADEMARK OFFICE
CERTIFICATE OF CORRECTION

PATENT NO. : 4,132,745
DATED : January 2, 1979
INVENTOR(S) : PIERRE AMIGUES ET AL It is certified that error appears in the above-identified patent and that said Letters Patent are hereby corrected as shown below:

Foreign Application Priority Data: reads " Jun. 25, 1976 [BE] Belgium...............19661 "

Should read -- Jun. 25, 1976 [FR] France ...... .......76/19.661 --.

Signed and Sealed this

Sixteenth Day of September 1980

[SEAL]

Attest:

SIDNEY A. DIAMOND

Attesting Officer     Commissioner of Patents and Trademarks